United States Patent [19]

Goto et al.

[11] Patent Number: 4,978,761
[45] Date of Patent: Dec. 18, 1990

[54] 5-HYDROXY-2-SUBSTITUTED-2,4,6,7-TET-RAMETHYL-2,3-DIHYDROBENZOFURANS

[75] Inventors: Giichi Goto; Shigenori Ohkawa, both of Osaka; Naohisa Fukuda, Kawanishi, all of Japan

[73] Assignee: Takeda Chemical Industries, Ltd., Osaka, Japan

[21] Appl. No.: 363,729

[22] Filed: Jun. 9, 1989

[30] Foreign Application Priority Data

Jun. 10, 1988 [JP] Japan .................. 63-143859

[51] Int. Cl.$^5$ ................................ C07D 307/79
[52] U.S. Cl. ...................... 549/462; 544/61; 544/153; 546/269; 548/203; 548/336; 549/458; 549/470
[58] Field of Search ................ 549/458, 462, 470

[56] References Cited

U.S. PATENT DOCUMENTS

| 2,318,895 | 5/1943 | Smith ............................ 549/462 |
| 2,411,942 | 12/1946 | Smith et al. ..................... 549/462 |
| 2,421,811 | 6/1947 | Smith et al. ..................... 549/462 |
| 2,554,687 | 5/1951 | Thompson et al. ............. 260/398.5 |
| 4,857,516 | 8/1989 | Terao et al. ..................... 514/469 |

FOREIGN PATENT DOCUMENTS 63-88173  4/1988  Japan .

OTHER PUBLICATIONS

Smith et al., J.A.C.S. 63, pp. 1887–1890 (1941).
Smith et al., J.S.C.S. 65, pp. 1594–1599 (1943).
Smith, et al., J. Org. Chem. 6, pp. 229–235 (1941).
Golumbic, J.A.C.S., 63, p. 1142 (1941).
Karrer et al., Helvetica Chimica Acta, vol. 31, No. 6, pp. 1505–1513 (1948).
Yutaka Maruyama et al., "5-Lipoxyggenase Inhibitors for the Treatment of Inflammation and Allergy", Chemical Abstracts, vol. 108, No. 10, Mar. 7, 1988, p. 445, Abstract No. 82107a.
Katsuji Ejiri et al., "Dihydrobenzofuran Derivatives as Antioxidants and drug Intermediates", Chemical Abstracts, vol. 110, Feb. 27, 1989, p. 630, Abstract No. 75294x.
CPI Abstract 4854619 WPI Acc. No. 88-145145/21, Abstract of JP-A-88173/1988.
Burton, Graham W., et al., "Antioxidant Activity of Phenols Related to Vitamin E. Are There Chain-Breaking Antioxidants Better Than α-Tocopherol?", J. Am. Chem. Soc., vol. 105, pp. 5950–5951 (1983).
Burton, Graham W., et al., "Autoxidation of Biological Molecules, 4, Maximizing the Antioxidant Activity of Phenols." J. Am. Chem. Soc., vol. 107, pp. 7053–7065 (1985).
Okamoto, Kayoko et al., "Synthesis of Quinones having Carboxy- and Hydroxy-Alkyl Side Chains, and Their Effects on Rat-Liver Lysosomal Membrane", Chem. Pharm. Bull., vol. 30, No. 8, pp. 2797–2819 (1982).
Ingold, K. U., et al., "A New Vitamin E Analogue More Active than α-Tocopherol in the Rat Curative Myopathy Bioassay", Febs Letters, vol. 205, No. 1, pp. 117–120 (1986).
S. Brownstein et al., "Chiral Effects on the 13C Resonances of Alpha-tocophrol and Related Compounds, A Novel Illustration of Newman's Rule of Six", Journal of Organic Chemistry, vol. 54, No. 3, Feb. 3, 1989, pp. 560–569.

Primary Examiner—Mary C. Lee
Assistant Examiner—Bernard I. Dentz
Attorney, Agent, or Firm—Wegner, Cantor, Mueller & Player

[57] ABSTRACT

The present invention relates to a compound of the formula:

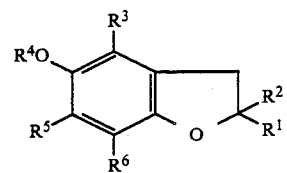

wherein $R^1$ is hydrogen or a lower alkyl; $R^2$ is methyl which is substituted by a carboxy, alkoxycarbonyl, cyano, halogen, aryl or heterocyclic group of $C_{2-15}$ chain hydrocarbon residue having no lower alkyl at the α-position which may be substituted by a carboxy, alkoxycarbonyl, cyano, halogen, aryl or heterocyclic group; $R^3$ is a lower alkyl; $R^4$ is hydrogen or acyl; and $R^5$ and $R^6$ each is a lower alkyl or lower alkoxy, or $R^5$ and $R^6$ combinedly are butadienylene or a salt thereof.

The compound (I) of the present invention has a strong 5- and 12-lipoxygenase inhibiting action, is of high safety and is useful as, among others, an agent for ameliorating dysfunction circulatory system, an anti-allergic agent and a pharmaceutical agent for central nervous system.

3 Claims, No Drawings

5-HYDROXY-2-SUBSTITUTED-2,4,6,7-TETRAMETHYL-2,3-DIHYDROBENZOFURANS

This invention relates to 2-substituted coumaran derivatives.

The present inventors synthesized various types of coumaran derivatives and found that they had inhibitory actions on 5-lipoxygenase and 12-lipoxygenase participating in the biosynthesis of leucotrienes and lipoxins, and they have continued the research work diligently to accomplish the present invention.

The present invention is to provide a compound of the formula:

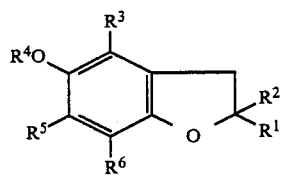
(I)

wherein $R^1$ is hydrogen or a lower alkyl; $R^2$ is methyl which is substituted by a carboxy, alkoxycarbonyl, cyano, halogen, aryl or heterocyclic group or $C_{2-15}$ chain hydrocarbon residue having no lower alkyl at the α-position which may be substituted by a carboxy, alkoxycarbonyl, cyano, halogen, aryl or heterocyclic group; $R^3$ is a lower alkyl; $R^4$ is hydrogen or acyl; $R^5$ and $R^6$ each is a lower alkyl or lower alkoxy, or $R^5$ and $R^6$ combinedly are butadienylene, and a salt thereof.

Referring to compounds represented by the above-mentioned (I), the lower alkyl represented by $R^1$ is exemplified by $C_{1-6}$ alkyl such as methyl, ethyl, propyl, i-propyl, butyl, i-butyl, sec-butyl, t-butyl, amyl, hexyl, etc., especially $C_{1-3}$ alkyl (methyl, ethyl, propyl, i-propyl, etc.) being preferable.

As substituents of the substituted methyl represented by $R^2$, mention is made of aryl (phenyl, 1-naphthyl, 2-naphthyl, indanyl, tetralyl, etc.), heterocyclic group (2-thienyl, 3-thienyl, 2-pyridyl, 3-pyridyl, 4-pyridyl, 1-imidazolyl, 5-thiazolyl, morpholino, thiomorpholino, etc), halogen (fluorine, chlorine, bromine, iodine), carboxyl, alkoxycarbonyl (preferably $C_{2-5}$ ones such as methoxycarbonyl, etc.), cyano, etc. Further, the aryl and the heterocyclic groups may have one or more substituents at an optional position of the ring. As the said substituents, mention is made of, for example, unsubstituted $C_{1-20}$ alkyl (e.g. methyl, ethyl, propyl, isopropyl, butyl, t-butyl, pentyl, hexyl, octyl, nonyl, decyl, undecyl, dodecyl, tridecyl, tetradecyl, pentadecyl, hexadecyl, heptadecyl, octadecyl, nonadecyl, eicosyl, etc.), lower ($C_{1-6}$) alkyl optionally substituted with a hydroxyl group, carboxyl, $C_{2-5}$ alkoxycarbonyl, piperazyl, phenylthio, etc., $C_{2-4}$alkenyl (vinyl, etc.) optionally substituted with a carboxyl or alkoxycarbonyl ($C_{2-5}$ alkoxycarbonyl such as methoxycarbonyl, ethoxycarbonyl, etc.), hydroxyl group, halogen (fluorine, chlorine, bromine, etc.), nitro, formyl, $C_{1-3}$ alkoxy (methoxy, etc.), carboxyl, trifluoromethyl, di-$C_{1-3}$ alkylamino, $C_{5-7}$ cycloalkyl, $C_{1-3}$ alkylthio, etc.

As the chain hydrocarbon residue having 2 to 15 carbon atoms, which has no lower alkyl on the α-position, represented by $R^2$, mention is made of straight-chain or branched $C_{2-15}$ chain aliphatic hydrocarbon groups, and when it is alkenyl, the number of double bonds is usually 1 to 5, and these double bonds may be conjugated. And, in the case of alkynyl, the number of its triple bonds is 1 to 5.

As the above-mentioned chain hydrocarbon residues, those having 2 to 6 carbon atoms are preferable, as exemplified by alkyl such as ethyl, i-propyl, butyl, i-butyl, sec-butyl, t-butyl, pentyl, hexyl, alkenyl and as 1-propenyl, 2-butenyl, 1,3-butadienyl, 2-pentenyl, vinyl 2-propenyl, isopropenyl, and alkynyl such as ethynyl, 2-propynyl, 2-penten-4-ynyl.

Referring to the substituents of $C_{2-15}$ chain hydrocarbon residue represented by $R^2$, as preferable alkoxycarbonyl, mention is made of $C_{2-5}$ alkoxycarbonyl (methoxycarbonyl, ethoxycarbonyl, propoxycarbonyl, i-propoxycarboxyl, etc.), and, as halogen, mention is made of fluorine, bromine, chlorine and iodine. For the aryl and heterocyclic groups, reference is made to the groups described above, and, for further substituents reference is made to the groups described above.

Examples of the lower alkyl represented by $R^3$ include $C_{1-6}$ alkyl such as methyl, ethyl, propyl, i-propyl, butyl, i-butyl, sec-butyl, t-butyl, amyl, hexyl, etc., especially, $C_{1-3}$ alkyls (methyl, ethyl, propyl, i-propyl, etc.) are preferable.

As the acyl represented by $R^4$, mention is made of acyl carboxylate, acyl sulfonate, acyl phosphate, etc., preferably those having $C_{1-10}$ substituents (methyl, ethyl, propyl, phenyl, etc.). Preferable ones include chain-like ($C_{1-10}$) or cyclic ($C_{3-10}$) alkanoyl, such as formyl, acetyl, propionyl, isobutyryl, decanoyl, cyclopentyl or cyclohexylcarbonyl, benzoyl, optionally quaterized nicotinoyl, half ester of succinate, etc.

Examples of the lower alkyl represented by $R^5$ and $R^6$ respectively include $C_{1-6}$ alkyl such as methyl, ethyl, propyl, i-propyl, butyl, i-butyl, sec-butyl, t-butyl, amyl, hexyl, etc., especially preferable ones being $C_{1-3}$ alkyl (methyl, ethyl, propyl, i-propyl, etc.). These substituents are exemplified by hydroxyl group, halogen (fluorine, bromine, chlorine, iodine, etc.), nitro, trifluoromethyl, carboxyl, $C_{2-5}$ alkoxycarboxyl (methoxycarbonyl, ethoxycarbonyl, etc.), 3-pyridyl, 1-imidazolyl, 5-thiazolyl, etc. And, examples of the lower alkoxy shown by $R^5$ and $R^6$ include $C_{1-3}$ alkoxy such as methoxy, ethoxy, propoxy, i-propoxy, etc.

When $R^5$ and $R^6$ combinedly represent butadienylene, a naphthalene ring is formed, and as the substituents on the thus-formed benzene ring, are mentioned one to three lower ($C_{1-3}$) alkyl, lower ($C_{1-3}$) alkoxy (methoxy, ethoxy, propoxy, etc.), hydroxyl groups, nitro, halogen, etc.

The compound (I) may, in accordance with the kinds of substituents thereon, form corresponding salts, and the salts are exemplified by those with an organic acid (e.g. acetic acid, propionic acid, oxalic acid, maleic acid) or an inorganic acid (e.g. hydrochloric acid, sulfuric acid, phosphoric acid, etc.), or those with a base such as an alkali metal (potassium, sodium, etc.), an alkaline earth metal (calcium, magnesium, etc.), ammonia, etc., and, among them, physiologically acceptable ones are especially preferable.

The compound (I) can be produced by, for example, allowing a compound represented by the formula

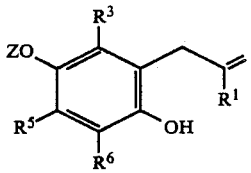

(II)

wherein $R^1$, $R^3$, $R^5$ and $R^6$ are of the same meaning defined as above, Z is hydrogen or a hydroxyl-protecting group, to react with a halogen molecule in the presence of a base to cause ring-closure, or by subjecting the compound (II) to the treatment with a peracid in the presence of a base to cause ring closure, followed by allowing the thus ring-closed compound to react with an oxidizing agent, then subjecting the thus-obtained compound to an addition-elimination reaction with a compound represented by the formula $$(C_6H_5)_3P^{\oplus}-R^2X^{\ominus} \quad (III)$$

wherein X is halogen, $R^2$ is a chain-like hydrocarbon residue whose carbon number is less by one than that of $R^2$, followed by, when desired, subjecting the resultant to deprotection, acylation, hydrogenation or(and) substituent-exchange reaction, respectively.

As the hydroxyl-protecting group, $C_{2-4}$ alkanoyl such as acetyl, propionyl, etc. is mentioned.

The ring-closure reaction with the aid of halogen is carried out by allowing, for example, bromine to react in an organic solvent such as a halogenated carbon (e.g. chloroform, methylene chloride, etc.) or acetic acid, etc. at temperatures ranging from $-5°$ C. to $80°$ C.

And, the cyanation can be carried out, in general, by allowing, for example, sodium cyanate or potassium cyanate to react in a solvent such as dimethyl sulfoxide, dimethyl formamide, etc. at temperatures ranging from $60°$ C. to $100°$ C. for 1 to 24 hours. In this case, the protecting group is hydrolyzed with a small volume of water present in the reaction system to give a 5-hydroxy compound at one stroke.

The ring-closure reaction by the use of a peracid is conducted by using a peracid such as m-chloroperbenzoic acid in an organic solvent such as methyl chloride in the presence of a base such as triethylamine at temperatures ranging from $-10°$ C. to $50°$ C. And, the oxidation is conducted by using an oxidizing agent obtained from dimethyl sulfoxide and oxalyl chloride, chromium trioxide, etc., in an organic solvent such as methylene chloride, acetone, etc., and, when desired, in the presence of a base such as triethylamine, etc., at temperatures ranging from $-78°$ C. to $25°$ C.

The addition-elimination reaction (Wittig reaction) is conducted by using, as the base, sodium hydride, sodium hydrobromide, sodium alcoholate, n-butyl lithium, lithium diisopropyl amide, etc., in a solvent such as dimethyl sulfoxide, tetrahydrofuran, dimethoxy ethane, etc. at temperatures ranging from $-78°$ C. to $80°$ C. for about 0.5 to 24 hours.

And, when the double bond is hydrogenated, the object compound can be obtained in accordance with a conventional method using a catalyst such as palladium-carbon, etc.

The elimination (hydrolysis) of the hydroxy-protecting group can be conducted under the conditions of conventional ester hydrolysis, but, when the product is unstable against oxygen under basic conditions, the reaction is conducted under argon atmosphere to thereby obtain the desired hydrolyzate in a good yield.

The acylation is carried out by using a desired acylating agent (acid anhydride, acid halogenide, etc.), when necessary, in the presence of a basic catalyst (preferably sodium hydride, potassium carbonate, pyridine and triethylamine) or an acid catalyst (sulfuric acid, hydrogen chloride, etc.), in an organic solvent (e.g. dimethylformamide, acetone, tetrahydrofuran) at temperatures ranging from about $-10°$ C. to $100°$ C. for about 10 minutes to 15 hours.

The compound thus obtained (I) can be isolated by conventional separation purification means (extraction, chromatography, recrystallization, etc.).

And, when the compound (I) exists in the state of a diastereomer, the respective components can be isolated by the above-mentioned separation purification means.

And, when the compound (I) is an optically active compound, it can be resolved into the d-compound and l-compound by conventional means for optical resolution.

The starting compound (II) can be synthesized by, for example, the method described below. More specifically, the monoacetate (IV) of hydroquinone is allowed to react with aryl halogenide in the presence of a base to lead to allyl ether (V), followed by subjecting (V) to Claisen rearrangement to give (II).

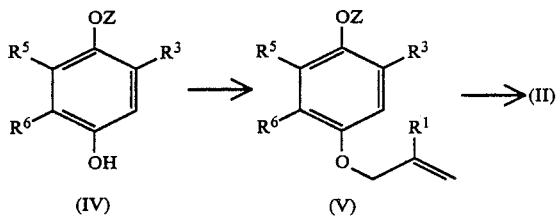

The compound (I) of this invention has an action of inhibiting production of 5-lipoxygenase-type metabolites [leucotrienes, 5-hydroperoxyeicosatetraenoic acid (HPETE), 5-hydroxyeicosatetraenoic acid (HETE), lipoxins, leucotoxins, etc.] and 12-lipoxygenase-type metabolites (12-HPETE, 12-HETE, etc.), and, therefore, the compound (I) can be used advantageously as an agent for ameliorating dysfunction of the circulatory system, an anti-allergic agent, and an agent acting on the central nervous system.

The compound (I) can be safely administered, orally or parenterally singly or as a pharmaceutical composition prepared by mixing the compound (I) with a per se known pharmaceutically acceptable carrier, excipient, etc. (e.g. tablet, capsule, liquid, injection, suppository), to mammals (rat, horse, cow, monkey, human, etc.). While the dosage varies with subjects of administration, administration routes, symptoms, etc., in the case of, for example, administering orally to an adult patient suffering from diseases of circulatory system, it is convenient to administer about 0.1 mg/kg to 20 mg/kg/body weight/dose, preferably 0.2 mg/kg to 10 mg/kg/body weight, once to three times a day.

Experimental Example 1:5-Lypoxygenase Inhibiting Action

In 0.5 ml of MCM (mast cell medium) was suspended $10^7$ of rat basophilic leukemia (RBL-1) cells. To this suspension was added the test solution previously prepared [consisting of 0.5 ml of MCM, 50 μg of arachidonic acid, 10 μg of calcium ionophore A-23187 and the test compound (final concentrations 10 μm, 1 μm, 0.1 μm and 0.01 μm)], and the reaction was allowed to proceed at 37° C. for 20 minutes. To the reaction mixture was added 4 ml of ethanol, which was shaken sufficiently, followed by leaving the resultant mixture standing for 10 minutes at room temperatures. The resultant mixture was subjected to a centrifuge (2000 rpm) for 10 minutes, then the supernatant was separated. Thus-separated supernatant was concentrated to dryness under reduced pressure. To the concentrate was added 0.5 ml of a 60% aqueous methanol. A 100μl Portion of this solution was taken and subjected to high performance liquid chromatography to perform quantitative determination of 5-HETE (5-hydroxyeicosatetraenoic acid). UV absorption of 5-HETE at 237 nm was measured with a UV absorption monitor. The inhibitory effect (IE) of 5-HETE is expressed by $(1-b/a) \times 100$. In this formula, a means the height of the peak or the area of the peak in the case of presence of no compound (I), while b means the height of the peak or the area of the peak in the case of presence of the compound (I). The results revealed, as shown in Table 1, that the test compounds showed strong inhibitory action on the production of 5-HETE.

TABLE 1

| | Effect of Inhibiting 5-Lipoxygenase | | | |
|---|---|---|---|---|
| | % Inhibition (IE) | | | |
| Compound | $10^{-5}M$ | $10^{-6}M$ | $10^{-7}M$ | $10^{-8}M$ |
| 5 | 100 | 100 | 57 | 0 |
| 6 | 100 | 100 | 52 | 4 |
| 10 | 100 | 99 | 98 | 12 |
| 12 | 100 | 100 | 90 | 46 |

Experimental Example 2

Through the descending aorta of a Wistar rat, 10 ml of blood was collected, under anesthesia, together with citric acid of a volume corresponding to 10%. PRP and PPP were respectively prepared, then they were mixed to make the number of platelets to be $10^9$/ml. To 2.5 μl each of the test solutions prepared in advance (final concentrations of the test compounds : 100 μm, 10 μm, 1 μm and 0.1 μm) was added 0.225 ml of the platelet solution. The respective solutions were kept at 37° C. for 5 minutes, to which was added 25 μl each of arachidonic acid solution (50 μg/ml) , then the respective mixtures were shaken immediately. The reaction was allowed to proceed at 37° C. for 15 minutes, and there was added ethanol (1 ml) to stop the reaction. The reaction mixture was subjected to a centrifuge (2000 rpm) for 5 minutes. One ml of the supernatant was taken, which was mixed with 1 ml of water. 100 μl of this mixture solution was subjected to high performance liquid chromatography to quantitatively determine 12-HETE. The detection was conducted at 240 nm. The calculation of the inhibition rate was conducted in a manner as in the case of 5-HETE. The results were shown in Table 2.

TABLE 2

| | 12-Lipoxygenase Inhibitory Action | | | |
|---|---|---|---|---|
| | % Inhibition (IE) | | | |
| Compound | $10^{-4}M$ | $10^{-5}M$ | $10^{-6}M$ | $10^{-7}M$ |
| 5 | 97 | 78 | 14 | — |
| 6 | 98 | 88 | 16 | 2 |
| 10 | 96 | 92 | 52 | 45 |
| 12 | 95 | 82 | 11 | — |

TABLE 2-continued

| | 12-Lipoxygenase Inhibitory Action | | | |
|---|---|---|---|---|
| | % Inhibition (IE) | | | |
| Compound | $10^{-4}M$ | $10^{-5}M$ | $10^{-6}M$ | $10^{-7}M$ |
| 15 | 100 | 100 | 99 | 25 |
| 17 | 100 | 99 | 98 | 22 |
| 18 | 100 | 100 | 89 | 18 |
| 20 | 100 | 99 | 97 | 9 |
| 21 | 100 | 100 | 98 | 21 |
| 23 | 100 | 100 | 92 | 19 |
| 24 | 100 | 99 | 98 | 13 |
| 26 | 100 | 99 | 28 | — |
| 27 | 100 | 100 | 99 | 19 |
| 29 | 100 | 99 | 58 | 7 |
| 30 | 100 | 100 | 98 | 21 |
| 32 | 99 | 99 | 45 | 2 |
| 33 | 100 | 100 | 28 | 2 |
| 35 | 99 | 99 | 49 | 8 |
| 36 | 100 | 100 | 100 | 97 |
| 37 | 100 | 100 | 31 | 2 |
| 38 | 99 | 99 | 90 | 3 |
| 39 | 100 | 100 | 32 | — |
| 40 | 99 | 96 | 48 | 6 |
| 41 | 99 | 74 | 20 | 9 |

EXAMPLES

By the following Reference Examples, Examples and Formulation Examples of the compounds of the present invention, the present invention will be described in a more concrete manner, but the present invention is not to be limited thereto.

REFERENCE EXAMPLE 1

To a solution of 4-acetoxy-2,3,5-trimethylphenol [20 g (103 mmol )] and methallyl chloride [10 g (110.4 mmol.)] in dimethylformamide (160 ml) was added potassium carbonate [15.2 g (110 mmol.)]. The mixture was stirred for 3 hours at 80° C. under argon atmosphere. The reaction mixture was, after cooling, diluted with water, and subjected to extraction with ethyl acetate. The extract was washed with water and dried, then the solvent was distilled off. The residue was crystallized from hexane to obtain the desired 4-acetoxy-2,3,5-trimethylphenyl-2-methylpropenylether [18.5 g (yield 72.4%)], m.p.44° to 45° C.

In a manner as above, 4-acetoxy-2,3,5-trimethylphenyl allyl ether was synthesized. (yield 76.7%, m.p. 40°-41° C.).

REFERENCE EXAMPLE 2

In N,N-diethylaniline (100 ml) was dissolved 4-acetoxy-2,3,5-trimethylphenyl 2-methylpropenylether [16.2 g (6.5 mmol)], which was heated at 200° C. for two hours. The reaction mixture was cooled and diluted with isopropyl ether, which was washed with 2N-HCl to remove N,N-diethylaniline. The remainder was washed with a saturated aqueous solution of sodium hydrogencarbonate, which was dried, followed by distilling off the solvent. The residue was crystallized from isopropylether-hexane to obtain the desired 4-acetoxy-2-(2-methyl-2-propenyl)-3,5,6-trimethylphenol [14.9 g (yield 91.7%)], m.p. 109°-110° C.

In a manner similar to the above, 4-acetoxy-2-allyl-3,4,6-trimethylphenol was synthesized. (Yield 94.6%, m.p. 117°-118° C.)

REFERENCE EXAMPLE 3

In methylene chloride (100 ml) was dissolved 4-acetoxy-2-(2-methyl-2-propenyl)-3,5,6-trimethylphenol

[30 g (40.3 mmol)]. To the solution was added at 0° C., in limited amounts, m-chloroperbenzoic acid [16.7 g (67.8 mmol)]. The reaction mixture was stirred for one hour, and there was added triethylamine (30 ml), followed by stirring for further one hour. The reaction mixture was washed with a saturated aqueous solution of sodium hydrogen carbonate, and then dried, followed by distilling off the solvent. The residue was crystallized from isopropyl ether-hexane to obtain the desired 5-acetoxy-2-hydroxymethyl-2,4,6,7-tetramethyl-2,3-dihydrobenzofuran [9.3 g (yield 87.4%, m.p. 98°-99° C.)].

REFERENCE EXAMPLE 4

To a methylene chloride solution (50 ml) of oxalyl chloride (2 ml) was added dropwise at −60° C. dimethylsulfoxide (4 ml). The mixture was stirred for 10 minutes, and there was then added dropwise a methylene chloride solution (10 ml) of 5-acetoxy-2-hydroxymethyl-2,4,6,7-tetramethyl-2,3-dihydrobenzofuran [5.0 g (19 mmol)]. The reaction mixture was stirred for 15 minutes, and there was added triethylamine (15 ml), and the mixture was stirred for further 10 minutes. The reaction mixture was washed with water and dried, followed by distilling off the solvent. The residue was crystallized from isopropylether-hexane to obtain 5-acetoxy-2-formyl-2,4,6,7-tetramethyl-2,3-dihydrobenzofuran (yield 96.7%), m.p. 78°-79° C.

EXAMPLE 1

To a chloroform (15 ml) solution of 4-acetoxy-2-allyl-3,5,6-trimethylphenol [2.0 g(8.5 mmol)] was added dropwise, while stirring, bromine [1.36 g (8.5 mmol)]. To the mixture was then added triethylamine (0.3 ml), which was heated for two hours under reflux. The reaction mixture was cooled, washed with water, dried and then concentrated. The concentrate was crystallized from hexane to obtain 5-acetoxy-2-bromoethyl-4,6,7-trimethyl-2,3-dihydrobenzofuran (Compound 14) [2.5 g(yield 93.2%)].

In a manner as above, 5-acetoxy-2-bromomethyl-2,4,6,7-tetramethyl-2,3-dihydrobenzofuran (Compound 13) was obtained from 4-acetoxy-3,5,6-trimethyl-2-(2-methyl-2-propenyl)phenol.

EXAMPLE 2

To a dimethyl sulfoxide (5 ml) solution of 5-acetoxy-2-bromomethyl-2,4,6,7-tetramethyl-2,3-dihydrobenzofuran [1.5 g(4.58 mmol)] was added sodium cyanide [270 mg (5.5 mmol)], and the mixture was stirred at 80° C. for 6 hours under argon atmosphere. The reaction mixture was, after cooling, diluted with water, and subjected to extraction with ethyl acetate. The extract was washed with water and dried, followed by distilling off the solvent. The residue was purified by means of a silica gel column chromatography [hexane - isopropyl ether (2:1)] to obtain 5-acetoxy-2,3-dihydrobenzofuran (Compound 6) (350 mg) and 5-acetoxy-2-cyanomethyl-2,4,6,7-tetramethyl-2,3-dihydrobenzofuran (Compound 5)(158 mg).

EXAMPLE 3

To a dimethylformamide (20 mol) solution of triethyl phosphonoacetate [2.7 g (12.1 mmol)] was added sodium hydride (content 60%)(504 mg), which was stirred for 15 minutes. To the reaction mixture was added a dimethyl formamide (5 ml) solution of 5-acetoxy-2-formyl-2,4,6,7-pentamethyl-2,3-dihydrobenzofuran [3.0 g (11.5 mmol)], and the mixture was stirred for further 30 minutes. The reaction mixture was diluted with water, and subjected to extraction with ethyl acetate. The extract solution was washed with water and dried, followed by distilling off the solvent. The residue was crystallized from hexane-isopropylether to obtain 3-(5-acetoxy-2,4,6,7-pentamethyl-2,3-dihydrobenzofuran-2-yl)acetic acid ethyl ester (Compound 4)(3.5 g). In a manner as above, Compound 8 was synthesized.

EXAMPLE 4

To a methanol (10 ml) solution of the ethyl ester of 3-(5-acetoxy-2,4,6,7-pentamethyl-2,3-dihydrobenzofuran-2-yl) acrylic acid [3.5 g (10.5 mmol)] was added a solution of sodium hydroxide (1.0 g) in water (5 ml). The mixture was heated for two hours under reflux under argon atmosphere. The reaction mixture was cooled and neutralized with 2N-HCl, and then subjected to extraction with isopropyl ether. The extract solution was washed with water and dried, followed by distilling off the solvent. The residue was crystallized from tetrahydrofuran - ethyl acetate to afford the desired 3-(5-acetoxy-2,4,6,7-pentamethyl-2,3-dihydrobenzofuran-2-yl)acrylic acid (Compound 3)(2.06 g). In a manner as above, Compounds 7 and 10 were synthesized.

EXAMPLE 5

To a solution of 3-(5-acetoxy-2,4,6,7-pentamethyl-2,3-dihydrobenzofuran-2-yl)acrylic acid (1.0 g) in acetic acid (10 ml) was added 5% palladium-carbon (0.4 g), and the mixture was subjected to hydrogenation for two hours at 80 C. The catalyst was then filtered off, which was followed by distilling off the solvent. The residue was crystallized from tetrahydrofuran-isopropyl ether (IPE) to afford the desired 3-(5-hydroxy-2,4,6,7-pentamethyl-2,3-dihydrobenzofuran-2-yl) propionic acid (Compound 2)(0.97 g). In a manner as above, Compounds 9 and 12 were obtained.

EXAMPLE 6

To a solution of 5-hydroxy-2-cyanomethyl-2,4,6,7-tetramethyl-2,3-dihydrobenzofuran in methanol (5 ml) was added a solution of sodium hydroxide (0.5 g) in water (5 ml). The mixture was heated for three hours under reflux under argon atmosphere. The reaction mixture was cooled to 0° C. neutralized with 2N-HCl. The reaction product was extracted with ethyl acetate. The extract solution was washed with water, dried and concentrated, and then crystallized from ethyl acetate - isopropyl ether to afford the desired 2-(5-hydroxy-2,4,6,7-tetramethyl-2,3-dihydrobenzofuran-2-yl)acetic acid (Compound 1) (0.1 g).

EXAMPLE 7

To a suspension of benzyltriphenyl phosphonium chloride [1.5 g (3.87 mmol)] in tetrahydrofuran (5 ml) was added dropwise, under ice-cooling, an n-butyl lithium hexane solution [(1.6M) 24 ml], followed by stirring for 15 minutes. To the reaction mixture was added a solution of 5-acetoxy-2-formyl-2,4,6,7-tetramethyl-2,3-dihydrobenzofuran (1.0 g) in tetrahydrofuran (3 ml). To the mixture was added water and it was subjected to extraction with ethyl acetate. The extract solution was washed with water and dried, then the solvent was distilled off. The residue was purified by means of a silica gel column chromatography [hexane-IPE(2:1)] to obtain the desired 5-acetoxy-2-cinnamoyl-2,4,6,7-tetramethyl-2,3-dihydrobenzofuran (Compound 11) (1.22 g).

Physico-chemical properties of the compounds obtained as above are shown in Table 3.

TABLE 3

Structure: benzofuran with $R^4O$-, three Me groups on the aromatic ring, and $R^2$, $R^1$ on the 2-position of the dihydrofuran ring.

| Compd. No. | $R^1$ | $R^2$ | $R^4$ | Yield (%) | m.p. (°C.) | NMR(δ ppm) CDCl$_3\phi$ |
|---|---|---|---|---|---|---|
| 1 | Me | —CH$_2$CO$_2$H | H | 22.7 | 184–185 | 1.47(3H), 1.98(3H), 2.03(6H), 2.63(2H), 2.80(1H), 3.20(1H), 4.00(1H), 7.10(1H); in DMSO-d$_6$ |
| 2 | Me | —(CH$_2$)$_2$CO$_2$H | H | 96.3 | 164–165 | 1.33(3H), 1.85(2H), 1.97(3H), 2.03(6H), 2.27(2H), 2.73(1H), 2.95(1H), 3.50(1H), 7.20(1H); in DMSO-d$_6$ |
| 3 | Me | —CH=CHCO$_2$H  E | H | 74.6 | 211–212 | 1.53(3H), 2.05(6H), 3.03(2H), 3.60(1H), 5.83(1H), 6.92(1H), 7.10(1H); in DMSO-d$_6$ |
| 4 | Me | —CH=CHCO$_2$Et  E | Ac | 92.0 | 91–92 | 1.27(3H), 1.58(3H), 1.95(3H), 2.00(3H), 2.13(3H), 2.30(3H), 3.07(2H), 4.17(2H), 6.02(1H), 7.05(1H) |
| 5 | Me | —CH$_2$CN | H | 11.7 | 127–128 | 1.63(3H), 2.10(6H), 2.68(2H), 2.95(1H), 3.17(1H), 4.20(1H) |
| 6 | Me | —CH$_2$Br | H | 26.8 | 101–102 | 1.60(3H), 2.12(9H), 2.88(1H), 3.27(1H), 3.48(2H), 4.15(1H) |
| 7 | Me | —(CH=CH)$_2$—CO$_2$H  E | H | 82.9 | 204–206 | 1.50(3H), 2.03(9H), 3.00(2H), 3.90(1H), 5.87(1H), 6.37(2H), 7.15(1H); in DMSO-d$_6$ |
| 8 | Me | —(CH=CH)$_2$—CO$_2$Et  E | Ac | 87.8 | — | 1.27(3H), 1.57(3H), 1.97(3H), 2.03(3H), 2.13(3H), 2.33(3H), 3.05(2H), 4.17(2H), 5.87(1H), 6.37(2H), 7.20(1H) |
| 9 | Me | —(CH$_2$)$_4$CO$_2$H | H | 74.0 | 143–144 | 1.28(3H), 1.50(6H), 1.93(3H), 2.00(6H), 2.20(2H), 2.72(1H), 2.93(1H), 7.20(1H); in DMSO-d$_6$ |
| 10 | Me | —CH=CH—Ph  E, Z | H | 95.1 | — | 1.52(3H), 1.87(3H), 2.00(3H), 2.07(3H), 2.88(1H), 3.18(1H), 4.08(1H), 5.90(1H), 6.48(1H), 7.23(5H) |
| 11 | Me | —CH=CH—Ph  E, Z | Ac | 95.2 | — | 1.57(3H), 1.90(6H), 1.97(3H), 2.30(3H), 2.88(1H), 3.20(1H), 5.90(1H), 6.50(1H), 7.25(5H) |
| 12 | Me | —(CH$_2$)$_2$—Ph | H | 85.7 | 80–81 | 1.47(3H), 1.98(2H), 2.13(6H), 2.15(3H), 2.73(2H), 2.87(1H), 3.05(1H), 4.08(1H), 7.23(5H) |
| 13 | Me | —CH$_2$Br | Ac | 91.0 | — | 1.60(3H), 2.00(6H), 2.10(3H), 2.30(3H), 2.90(1H), 3.30(1H), 3.50(2H) |
| 14 | H | —CH$_2$Br | Ac | 93.2 | 80–81 | 2.00(6H), 2.10(3H), 2.30(3H), 3.13(2H), 3.53(2H), 4.97(1H) |
| 15 | Me | —CH=CH—CH$_2$—Ph  Z | H | 70.4 | 62–63 | 1.57(3H), 2.11(3H), 2.16(3H), 2.18(3H), 3.06(1H), 3.20(1H), 3.56(1H), 3.69(1H), 4.16(1H), 5.56(1H), 5.75(1H), 7.15–7.35(5H) |
| 16 | Me | —CH=CH—CH$_2$—Ph  Z | Ac | 74.9 | oil | 1.60(3H), 2.00(6H), 2.08(3H), 2.32(3H), 3.05(1H), 3.23(1H), 3.56(1H), 3.67(1H), 5.50(1H), 5.75(1H), 7.23(5H,m) |
| 17 | Me | —CH=CH—CH$_2$—Ph  E | H | 50.0 | 97–98 | 1.52(3H), 2.10(3H), 2.12(3H), 2.14(3H), 2.95(1H), 3.10(1H), 3.38(2H), 4.15(1H), 5.74(1H), 5.84(1H), 7.10–7.40(5H,m) |
| 18 | Me | —CH=CH—Ph  E | H | 61.0 | 107–108 | 1.64(3H), 2.11(3H), 2.16(3H), 2.18(3H), 3.06(1H), 3.20(1H), 4.17(1H), 6.40(1H), 6.64(1H), 7.15–7.45(5H) |
| 19 | Me | —CH=CH—Ph  E | Ac | 92.0 | 103–105 | 1.63(3H), 1.97(3H), 2.02(3H), 2.15(3H), 2.30(3H), 3.00(1H), 3.23(1H), 6.33(1H), 6.65(1H), 7.20–7.50(5H) |
| 20 | Me | —(CH$_2$)$_3$—Ph | H | 93.3 | 92–93 | 1.37(3H), 1.72(4H), 2.07(6H), 2.10(3H), 2.62(2H), 2.77(1H), 2.97(1H), 4.07(1H), 7.00–7.35(5H) |
| 21 | Me | —CH=CH—(CH$_2$)$_2$—Ph  Z | H | 95.5 | 64–65 | 1.45(3H), 2.07(6H), 2.12(3H), 2.61(4H), 3.00(2H), 4.08(1H), 5.48(1H), 6.14(1H), 7.00–7.30(5H) |

TABLE 3-continued

Structure: benzofuran with R⁴O, Me substituents on ring, Me groups, and R¹, R² on the oxygen-containing ring.

| Compd. No. | R¹ | R² | R⁴ | Yield (%) | m.p. (°C.) | NMR(δ ppm) CDCl₃φ |
|---|---|---|---|---|---|---|
| 22 | Me | —CH=CH—(CH₂)₂—Ph (Z) | Ac | 57.6 | oil | 1.47(3H), 1.93(3H), 1.98(3H), 2.07(3H), 2.30(3H), 2.40-2.80(2H), 3.00(2H), 5.38(1H), 5.68(1H), 7.00-7.35(5H) |
| 23 | Me | —(CH₂)₄—Ph | H | 87.5 | 73-74 | 1.20-1.80(6H), 1.03(3H), 1.07(6H), 2.12(3H), 2.60(2H), 2.77(1H), 2.97(1H), 4.08(1H), 7.00-7.35(5H) |
| 24 | Me | —CH=CH—Ph-4-OMe (Z) | H | 97.0 | oil | 1.53(3H), 1.93(3H), 2.02(3H), 2.08(3H), 2.90(1H), 3.22(1H), 3.78(3H), 4.17(1H), 5.83(1H), 6.42(1H), 6.78(2H), 7.23(2H) |
| 25 | Me | —CH=CH—Ph-4-OMe (Z) | Ac | 81.1 | oil | 1.53(3H), 1.92(6H), 1.97(3H), 2.27(3H), 2.90(1H), 3.22(1H), 3.77(3H), 5.83(1H), 6.42(1H), 6.77(2H), 7.20(2H) |
| 26 | Me | —(CH₂)₂—Ph-4-OMe | H | 93.8 | 77-78 | 1.47(3H), 1.65-2.10(2H), 2.13(6H), 2.15(3H), 2.40-2.80(2H), 2.83(1H), 3.05(1H), 3.78(3H), 4.10(1H), 6.78(2H), 7.10(2H) |
| 27 | Me | —CH=CH—Ph-3-OMe (Z) | H | 98.0 | oil | 1.53(3H), 1.90(3H), 2.02(3H), 2.08(3H), 2.90(1H), 3.22(1H), 3.67(3H), 4.17(1H), 5.90(1H), 6.48(1H), 6.65-7.30(4H) |
| 28 | Me | —CH=CH—Ph-3-OMe (Z) | Ac | 92.6 | oil | 1.53(3H), 1.88(6H), 1.95(3H), 2.90(1H), 3.23(1H), 3.67(3H), 5.88(1H), 6.47(1H), 6.60-6.90(3H), 7.05-7.30(1H) |
| 29 | Me | —(CH₂)₂—Ph-3-OMe | H | 84.2 | 79-80 | 1.47(3H), 1.70-2.10(2H), 2.10(6H), 2.13(3H), 2.40-2.80(2H), 2.83(1H), 3.05(1H), 3.77(3H), 4.10(1H), 6.60-6.85(3H) 7.10-7.30(1H) |
| 30 | Me | —CH=CH—Ph-4-F (Z) | H | 94.6 | oil | 1.53(3H), 1.85(3H), 2.03(3H), 2.07(3H), 2.90(1H), 3.20(1H), 4.20(1H), 5.85(1H), 6.43(1H), 6.75-7.10(2H), 7.10-7.30(2H) |
| 31 | Me | —CH=CH—Ph-4-F (Z) | Ac | 88.8 | oil | 1.55(3H), 1.83(3H), 1.90(3H), 1.93(3H), 2.27(3H), 2.90(1H), 3.22(1H), 5.87(1H), 6.42(1H), 6.90(2H), 7.20(2H) |
| 32 | Me | —(CH₂)₂—Ph-4-F | H | 79.6 | 76-77 | 1.47(3H), 1.70-2.10(2H), 2.10(6H), 2.13(3H), 2.40-2.80(2H), 2.83(1H), 3.05(1H) 4.10(1H), 7.10(4H) |
| 33 | Me | —CH=CH—Ph-4-Me (Z) | H | 96.5 | oil | 1.53(3H), 1.90(6H), 1.97(3H), 2.28(3H), 2.33(3H), 2.90(1H), 3.22(1H), 5.87(1H), 6.47(1H), 6.95-7.25(4H) |
| 34 | Me | —CH=CH—Ph-4-Me (Z) | Ac | 91.1 | oil | 1.53(3H), 1.90(3H), 2.00(3H), 2.07(3H), 2.88(1H), 3.20(1H), 4.10(1H), 5.87(1H), 6.43(1H), 6.90-7.30(4H) |
| 35 | Me | —(CH₂)₂—Ph-4-Me | H | 80.5 | 106-107 | 1.47(3H), 1.70-2.10(2H), 2.10(6H), 2.13(3H), 2.40-2.80(2H), 2.83(1H), 3.05(1H), 4.10(1H), 7.10(4H) |
| 36 | Me | —CH=CH—(CH₂)₂Me (Z) | H | 41.5 | oil | 0.91(3H), 1.40(2H), 1.52(3H), 2.12(6H), 2.17(3H), 2.19(2H), 3.04(2H), 3.16(1H), 4.16(1H), 5.38(1H), 5.68(1H) |
| 37 | Me | —(CH₂)₄Me | H | 90.4 | 59-60 | 0.88(3H), 1.29(6H), 1.39(3H), 1.68(6H), 2.10(6H), 2.13(3H), 2.81(1H), 2.97(1H), 4.14(1H) |
| 38 | Me | —CH=CH—(CH₂)₆Me (Z) | H | 49.7 | oil | 0.88(3H), 1.26(10H), 1.51(3H), 2.12(6H), 2.14(3H), 2.20(2H), 3.04(2H), 3.16(1H), 4.15(1H), 5.38(1H), 5.66(1H) |
| 39 | Me | —(CH₂)₈Me | H | 83.3 | 69-70 | 0.88(3H), 1.26(14H), 1.39(3H), 1.70(2H), 2.10(6H), 2.13(3H), 2.81(1H), 2.97(1H), 4.13(1H) |
| 40 | Me | —CH=CH—(CH₂)₁₀Me (Z) | H | 45.8 | oil | 0.88(3H), 1.25(18H), 1.51(3H), 2.11(6H), 2.14(3H), 2.20(2H), 3.04(2H), 3.16(1H), 4.14(1H), 5.38(1H), 5.66(1H) |
| 41 | Me | —(CH₂)₁₂Me | H | 84.6 | 67-68 | 0.88(3H), 1.25(22H), 1.39(3H), 1.68(2H), 2.10(6H), 2.13(3H), 2.81(1H), |

TABLE 3-continued

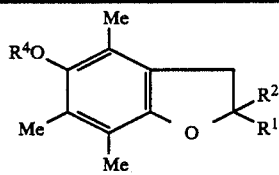

| Compd. No. | R¹ | R² | R⁴ | Yield (%) | m.p. (°C.) | NMR(δ ppm) CDCl₃φ |
|---|---|---|---|---|---|---|
| | | | | | | 2.97(1H), 4.14(1H) |

Me: Methyl,
Ac: Acetyl,
Ph: Phenyl

Formulation Examples

| (A) Soft capsule | | |
|---|---|---|
| (1) Compound 3 | | 50 mg |
| (2) Corn oil | | 100 mg |
| | total | 150 mg |

By a conventional method, (1) and (2) were mixed, which was filled in a capsule.

(B) Tablet

| (B) Tablet | |
|---|---|
| (1) Compound 10 | 50 mg |
| (2) Lactose | 30 mg |
| (3) Corn starch | 10.6 mg |
| (4) Corn starch (paste) | 5 mg |
| (5) Magnesium stearate | 0.4 mg |
| (6) Carboxymethyl cellulose sodium | 20 mg |
| total | 120 mg |

By a conventional method, these were mixed, which are tableted by a tablet machine.

We claim:

1. 5-Hydroxy-2-(phenyl-aliphatic)-2,4,6,7-tetramethyl-2,3-dihydrobenzofuran wherein said aliphatic is $C_{2-6}$ alkylene or $C_{2-6}$ alkenylene and said phenyl is unsubstituted or substituted by $C_{1-3}$ alkyl, $C_{1-3}$ alkoxy or halogen, or a pharmaceutically acceptable salt thereof.

2. The compound 5-hydroxy-2-cinnamyl-2,4,6,7-tetramethyl-2,3-dihydrobenzofuran.

3. The compound 5-hydroxy-2-phenylethyl-2,4,6,7-tetramethyl-2,3-dihydrobenzofuran.

* * * * *